US00PP34207P2

(12) United States Plant Patent
Bradford et al.

(10) Patent No.: US PP34,207 P2
(45) Date of Patent: May 10, 2022

(54) PLUM TREE NAMED 'PLUMSWEET XXV'

(50) Latin Name: *Prunus salicina*
Varietal Denomination: PLUMSWEET XXV

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 0 days.

(21) Appl. No.: 17/300,919

(22) Filed: Dec. 17, 2021

(51) Int. Cl.
*A01H 5/08* (2018.01)
*A01H 6/74* (2018.01)

(52) U.S. Cl.
USPC ..... Plt./184

(58) Field of Classification Search
USPC ..... Plt./180, 184
See application file for complete search history.

(56) References Cited

U.S. PATENT DOCUMENTS

PP19,591 P2 12/2008 Bradford
PP20,892 P2 3/2010 Bradford

*Primary Examiner* — Susan McCormick Ewoldt

(57) ABSTRACT

The present invention relates to a plum tree, *Prunus salicina*, and more particularly to a new and distinct variety broadly characterized by a medium size, vigorous, hardy, and productive tree. Being self-unfruitful, the present variety requires cross pollination from an apricot, interspecific, or plum that blooms during the late season, such as 'Plumred VII' interspecific tree (U.S. Plant Pat. No. 23,688). The present variety produces a heavy density of flowers that produce a moderate amount of pollen to entice good bee activity to facilitate pollination. The fruit matures under the ecological conditions described during late August, with first picking on Aug. 22, 2021. The fruit is uniformly large in size, globose to oblate in shape, very deep purplish red with heavy freckling in skin color, full red flesh in color, clingstone in type, firm and crisp in texture, juicy, very sweet, excellent in flavor, and virtually non-acidic in both the flesh and skin.

1 Drawing Sheet

Botanical classification: *Prunus salicina.*
Varietal denomination: 'PLUMSWEET XXV'.

BACKGROUND OF THE VARIETY

In a continuing effort to improve the quality of shipping fruits, we, the inventors, typically hybridize a large number of peach, nectarine, plum, apricot, and cherry seedlings each year. We also grow a lesser number of open pollinated seeds of each of these fruits. The present invention relates to a new and distinct variety of plum tree which has been denominated varietally as 'PLUMSWEET XXV'.

Each blooming season we perform interfertile checks on our newest and best plum and interspecific varieties. These tests are done by tying several paper bags over short limbs on a selected mother tree just before the onset of bloom. When the tree reaches between seventy-five to one hundred percent bloom, each bag is removed for a very short time while we apply pollen by hand from one of our other varieties that might be a potential pollinator. The bag is carefully replaced to the same position to prevent any other pollen from reaching these flowers by another method, such as bees or wind. Each bag is carefully labeled with a tag indicating its pollen identity. The bags are left on the tree until petal fall, and then they are torn open to allow the fruit to grow normally. When the fruit reaches about ½" [12.7 mm.] in diameter, the number of successfully pollinated flowers can then be counted and recorded. The results can range between zero and up to fifty, with 5 or higher indicating a good pollinator. Because these trials are also very good crosses, we usually grow their seeds separated only by early, medium and late harvesting.

During the latter part of the 2014 fruit season, we gathered the fruit from our late ripening interfertile trials, which consisted of about 700 fruits from 80 different combinations. We then removed, stratified and germinated the seeds as a group with the label "Late Bags". They were grown as seedlings on their own root in our greenhouse, and upon reaching dormancy they were transplanted to a cultivated area of our experimental orchard located near Le Grand, Calif. in Merced County (San Joaquin Valley). During the summer of 2019 the claimed variety was selected by us as a single plant from the group of seedlings described above. Subsequent to origination of the present variety of plum tree, we asexually reproduced it by budding and grafting in the experimental orchard described above, and such reproduction of plant and fruit characteristics were true to the original tree in all respects. The reproduction of the variety included the use of 'Nemaguard' (unpatented) rootstock upon which the present variety was compatible and true to type.

The present variety is most similar to 'Plumred XIV' plum tree (U.S. Plant Pat. No. 33,139), by being self-unfruitful and by producing fruit that is mostly globose in shape, fairly large in size, dark purplish red in primary skin color, entirely red in flesh color, firm and crisp in texture, juicy, very sweet, excellent in flavor, and clingstone in type, but is distinguished therefrom by blooming later and by producing fruit that has much heavier and larger skin freckling, that has much less skin and flesh acidity, and that matures about two weeks later.

SUMMARY OF VARIETY

The present plum variety is characterized by a medium size, vigorous, hardy, and productive tree. Being self-unfruitful, the present variety requires cross pollination from an apricot, interspecific, or plum that blooms during the late season, such as 'Plumred VII' interspecific tree (U.S. Plant Pat. No. 23,688). The present variety produces a heavy density of flowers that produce a moderate amount of pollen to entice good bee activity to facilitate pollination. The fruit matures under the ecological conditions described during late August, with first picking on Aug. 22, 2021. The fruit is uniformly large in size, globose to oblate in shape, very deep purplish red with heavy freckling in skin color, full red flesh in color, clingstone in type, firm and crisp in texture, juicy, very sweet, excellent in flavor, and virtually non-acidic in both the flesh and skin.

DRAWING

The accompanying photograph consists of four whole fruits positioned to display the characteristics of the skin color and form, one divided fruit to reveal the flesh and stone, typical leaves, and two insets depicting the flower buds and blossoms as they appeared on the tree during the blooming season.

POMOLOGICAL CHARACTERISTICS

Referring now more specifically to the pomological characteristics of this new and distinct variety of plum tree, the following has been observed under the ecological conditions prevailing near Le Grand, Merced County (San Joaquin Valley), Calif. The fruit description was developed at the state of firm ripe on Aug. 27, 2021, on the original tree during its seventh growing season. The flower and bud descriptions were developed during the previous blooming season. All major color code designations are by reference to the Inter-Society Color Council, National Bureau of Standards. Common color names are also used occasionally.

PARENTAGE

Seed parent: Unknown plum.
Pollen parent: Unknown plum.

TREE

Size: Medium, reaching and maintaining a height of 12' [3.66 m.] and a spread of 9' [2.74 m.] after seven growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Upright and dense.

Form: Pruned to a vase shape.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Very productive, thinning usually necessary.

Fertility: Self-unfruitful, requiring cross pollination by a suitable mid to late seasonal blooming interspecific or plum, such as 'Plumred VII' interspecific tree (U.S. Plant Pat. No. 23,688).

Bearing: Regular bearer, weather dependent, no crop failures observed as of yet.

Trunk:

*Size*.—Medium, reaching a maximum diameter of 4½" [114 mm.] after the seven growing season.

*Texture*.—Rough.

*Bark color*.—A Light grayish brown [60. l.gy.Br] and Grayish brown [61. gy.Br] variegation with Strong brown [55. s.Br] crevices present.

*Lenticels*.—Approximate Number Per Square Inch: 6. Color: Brownish orange [54. brO]. Average Size: ¼" [6.4 mm.] in length. The width is typically one fourth as much as the length. Shape: Elongated.

Branches:

*Size*.—Slender, scaffold diameter is 2½" [63.5 mm.] measured 12" above the crotch, limb diameter is 1¼" [31.8 mm.] measured 12" above the first fork.

*Texture*.—Smooth to medium on first and second year wood, increasing roughness with age.

*Color*.—1st Year Wood Topside: Grayish red [19. gy.R]. 1st Year Wood Underside: Brilliant yellow green [116. brill.YG]. Older Wood: A Grayish brown [61. gy.Br] and Moderate yellowish brown [77. m.yBr] variegation with Light grayish brown [60. l.gy.Br] crevices present.

*Lenticels*.—Number Per Square Inch: About 20 on second year wood. Color: Dark orange yellow [72. d.OY]. Average Size: Small, 1/16" [1.6 mm.] in length. The width is typically one fourth as much as the length. Shape: Elongated.

Leaves:

*Size*.—Medium. Average Length: 4 3/16" [106 mm.]. Average Width: 2" [50.8 mm.].

*Arrangement*.—Alternate.

*Thickness*.—Medium.

*Form*.—Elliptical.

*Apex*.—Acuminate.

*Base*.—Acute with an average base angle of 70 degrees.

*Surface*.—Smooth.

*Color*.—Dorsal Surface: Moderate olive green [125. m.OlG]. Ventral Surface: Moderate yellow green [120. m.YG].

*Margin*.—Finely serrate.

*Venation*.—Pinnately net veined.

*Petiole*.—Average Length: 11/16" [17.5 mm.]. Average Thickness: 1/16" [1.6 mm.]. Color: Light yellow green [119. l.YG] with some Grayish red [19. gy.R] areas where exposed toward the sun.

*Stipules*.—Number: Mostly 2 per leaf, up to 6 per growing tip. Average Length: ¼" [6.4 mm.]. Color: Vivid yellow green [115. v.YG] becoming Grayish red [19. gy.R] with age.

*Glands*.—Number: Mostly 2 per leaf. Position: Alternate, positioned at the intersection of the petiole and base of leaf blade. Form: Globose. Size: Medium, 1/32" [0.8 mm.] in diameter. Color: Light yellow green [119. l.YG] becoming Deep yellowish brown [75. deep yBr] in the center with age. Leaf buds: Pointed.

Flower buds:
*Hardiness*.—Hardy with respect to central California blooming season.
*Diameter*.—Typically 3/16" [4.8 mm.] 1 week before bloom.
*Length*.—Typically 3/8" [9.5 mm.] 1 week before bloom.
*Form*.—Not appressed.
*Surface*.—Very slightly pubescent.
*Tip color*.—Light pink [4. l.Pk].

Flowers: Perfect, complete, perigynous, usually a single pistil, typically thirty or more stamens, five sepals and petal locations alternately positioned.
*Average flower diameter*.—1 1/4" [31.8 mm.].
*Average flower depth*.—5/16" [7.9 mm.] when fully open.
*Average pedicel length*.—3/8" [9.5 mm.].
*Number of petals*.—Five, no double blossoms observed.
*Petal arrangement*.—Non-overlapping at full bloom.
*Petal shape*.—Oval.
*Petal margin*.—Entire, slightly wavy.
*Average petal diameter*.—7/16" [11.1 mm.].
*Average petal length*.—5/8" [15.9 mm.].
*Petal apex*.—Rounded.
*Petal base*.—Rounded to slightly acute.
*Petal color*.—White [263. White] on both sides with a slight amount of Pale pink [7. p.Pk] tinting on some.
*Anther color*.—Light yellow [86. l.Y].
*Pollen production*.—Medium, enticing to bees.
*Pollen color*.—Brilliant yellow [83. brill.Y].
*Stigma color*.—Light greenish yellow [101. l.gY].
*Stigma position*.—Located slightly above the surrounding anthers.
*Stamen position*.—Typically located about 1/32" [0.8 mm.] below the petals.
*Average pistil length*.—11/16" [17.5 mm.].
*Average stamen length*.—7/16" [11.1 mm.].
*Ovary*.—Non-pubescent.
*Sepal color*.—Light yellow green [119. l.YG] on both sides.
*Sepal outer surface*.—Fairly smooth to very slightly pubescent.
*Sepal length*.—3/16" [4.8 mm.].
*Sepal width*.—1/8" [3.2 mm.].
*Sepal apex*.—Rounded to elliptical to match the width and length.
*Sepal margin*.—Finely serrate.
*Fragrance*.—Moderate.
*Bloom density*.—Heavy.
*Number per cluster*.—2 to 7.
*Blooming period*.—Late compared to other varieties, blooms about two days before 'September Yummy' (U.S. Plant Pat. No. 14,220) plum tree.
*Onset of bloom*.—One percent on Feb. 25, 2021.
*Date of full bloom*.—Mar. 6, 2021.
*Duration of bloom*.—One to two weeks, dependent on ambient temperature.

FRUIT

Maturity when described: Firm ripe, Aug. 27, 2021.
Date of first picking: Aug. 22, 2021.
Date of last picking: Sep. 7, 2021.
Size: Uniform, large.
*Average diameter axially*.—2 3/4" [69.9 mm.].
*Average diameter across cheek plane*.—2 7/8" [73.0 mm.].
*Average diameter across suture plane*.—2 13/16" [71.4 mm.].
*Typical weight*.—7.3 ounces [207 grams].

Form: Fairly uniform, globose to oblate, mostly symmetrical.
*Longitudinal section form*.—Round to oblate.
*Axial view form*.—Round.

Suture: A distinct Light grayish purplish red [261. l.gy.pR] line located in a shallow trough extending from the base to the apex.
Ventral surface: Rounded, lipped on both sides.
Lips: Mostly equal.
Cavity: Flaring.
*Depth*.—7/16" [11.1 mm.].
*Breadth*.—1 1/4" [31.8 mm.].
Base: Truncate, somewhat cordate if viewed parallel to the suture.
Apex: Mostly rounded with some slightly protruding.
Pistil point: Apical, an inconspicuous Moderate greenish yellow [102. m.gY] dot located at the end of the suture, negligible in length.
Stem: Medium.
*Average length*.—3/8" [9.5 mm.].
*Average width*.—3/32" [2.4 mm.].

Skin:
*Thickness*.—Medium.
*Surface*.—Smooth.
*Tenacity*.—Tenacious to the flesh.
*Astringency*.—Very slight to none.
*Tendency to crack*.—None observed.
*Color*.—Very deep purplish red [257. v.deep pR] with heavy Moderate greenish yellow [102. m.gY] freckling throughout.

Flesh:
*Color*.—Very deep red [14. v.deep R] toward the skin smoothly blending to Dark reddish orange [38. d.rO] toward the stone.
*Surface of pit cavity*.—Covered with Dark red [16. d.R] fibers when twisted from the stone.
*Amygdalin*.—Scarce to non-existent.
*Juice*.—Abundant, rich.
*Texture*.—Firm, crisp.
*Fibers*.—Abundant, fine, tender.
*Ripens*.—Fairly even.
*Flavor*.—Very sweet with virtually no acid, typically 22 brix.
*Aroma*.—Very slight.
*Eating quality*.—Outstanding.

STONE

Type: Clingstone.
Form: Oval.
Hilum: Narrow.
Base: Slightly rounded to truncate.
Apex: Acute.
Tip: Sharp, about 1/32" [0.8 mm.] in length.
Sides: Mostly equal.
Surface: Fairly smooth with rounded ridges toward the base.
External color of stone: Light brown [57. l.Br].
Pit wall color when cracked: Moderate orange [53. m.O].
Cavity surface color: Light brown [57. l.Br].
Average pit wall thickness: 3/32" [2.4 mm.].
Average length: 1" [25.4 mm.].
Average width: 11/16" [17.5 mm.].
Average breadth: 7/16" [11.1 mm.].
Tendency to split: None observed.

Kernel:

*Form*.—Oval.

*Skin color*.—Light yellowish brown [76. l.yBr].

*Pellicle color*.—Deep yellowish brown [75. deep yBr].

*Vein color*.—Strong yellowish brown [74. s.yBr].

*Taste*.—Slightly bitter.

*Viable*.—Yes.

*Average length*.—5/8" [15.9 mm.].

*Average width*.—7/16" [11.1 mm.].

*Amygdalin*.—Moderate.

USE

Market: Fresh market and long distance shipping.

Keeping quality: Good, fruit quality observed to remain in good condition after 21 days in standard cold room at 36° Fahrenheit [2° Celsius].

Shipping quality: Good.

Resistance to insects: No unusual susceptibilities noted.

Resistance to diseases: No unusual susceptibilities noted.

OTHER NOTES

Although the new variety of plum tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of plum tree, *Prunus salicina*, substantially as illustrated and described, that is most similar to 'Plumred XIV' plum tree (U.S. Plant Pat. No. 33,139), by being self-unfruitful and by producing fruit that is mostly globose in shape, fairly large in size, dark purplish red in primary skin color, entirely red in flesh color, firm and crisp in texture, juicy, very sweet, excellent in flavor, and clingstone in type, but is distinguished therefrom by blooming later and by producing fruit that has much heavier and larger skin freckling, that has much less skin and flesh acidity, and that matures about two weeks later.

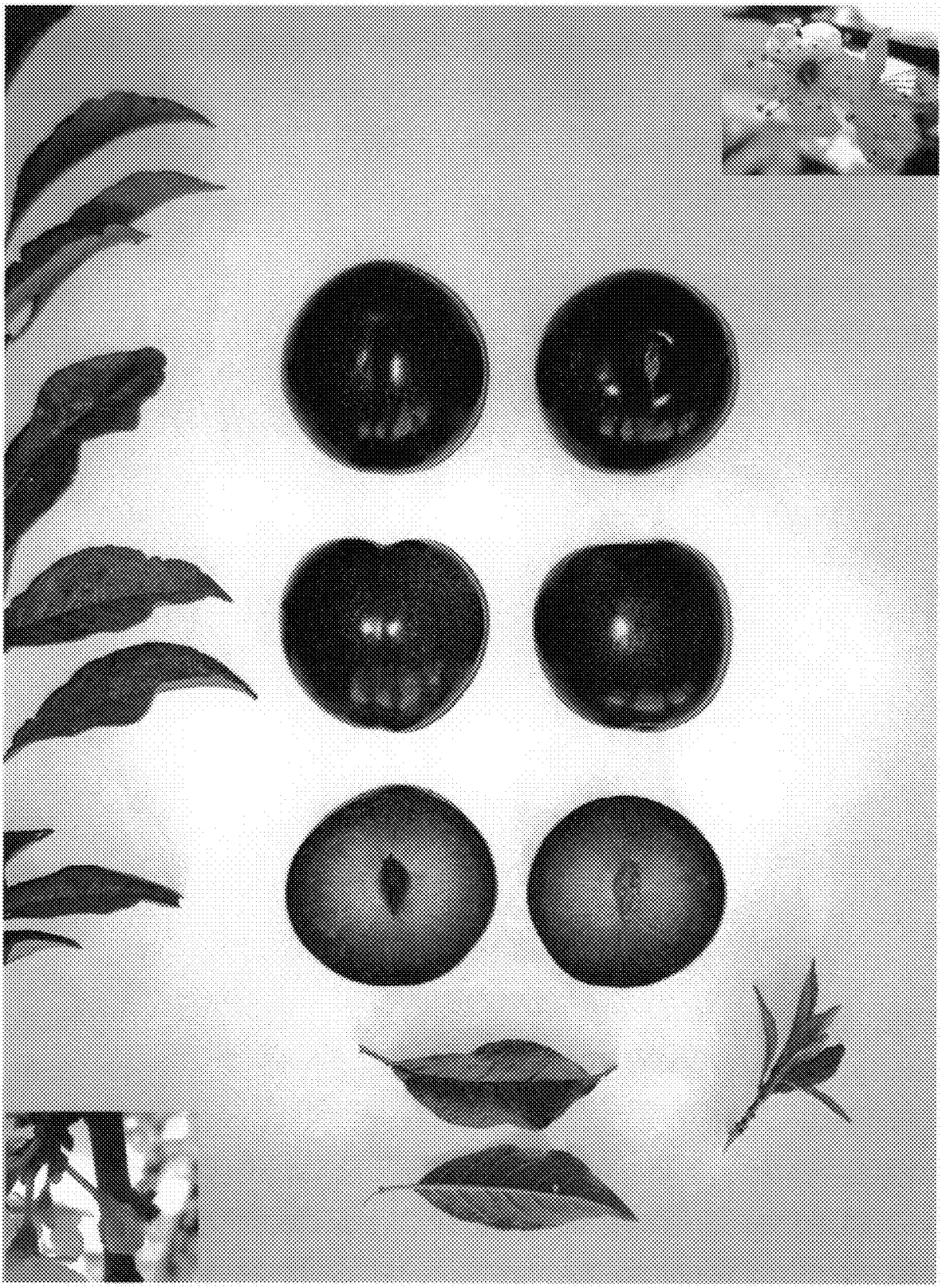

* * * * *